United States Patent
Porter

[19]

[11] Patent Number: 6,042,535
[45] Date of Patent: Mar. 28, 2000

[54] FLOW-AROUND VALVE

[75] Inventor: Christopher H. Porter, Woodinville, Wash.

[73] Assignee: SRS Medical Systems, Inc., Burlington, Mass.

[21] Appl. No.: 08/896,072

[22] Filed: Jul. 17, 1997

[51] Int. Cl.[7] ........................................................ A61F 2/02
[52] U.S. Cl. ................................ 600/31; 128/DIG. 25
[58] Field of Search ................. 600/29–31; 128/DIG. 25

[56] References Cited

U.S. PATENT DOCUMENTS

| | | | |
|---|---|---|---|
| 2,494,393 | 1/1950 | Lamson | 600/29 |
| 3,583,391 | 6/1971 | Cox et al. . | |
| 3,750,194 | 8/1973 | Summers . | |
| 3,841,304 | 10/1974 | Jones | 600/29 |
| 3,908,635 | 9/1975 | Viek . | |
| 4,386,601 | 6/1983 | Trick . | |
| 4,419,985 | 12/1983 | Trick . | |
| 4,822,333 | 4/1989 | Lavarenne . | |
| 4,932,938 | 6/1990 | Goldberg et al. . | |
| 4,994,066 | 2/1991 | Voss . | |
| 5,030,199 | 7/1991 | Barwick et al. . | |
| 5,088,980 | 2/1992 | Leighton | 600/30 |
| 5,090,424 | 2/1992 | Simon et al. | 600/29 |
| 5,112,306 | 5/1992 | Burton et al. . | |
| 5,114,398 | 5/1992 | Trick et al. . | |
| 5,306,241 | 4/1994 | Samples . | |
| 5,483,976 | 1/1996 | McLaughlin et al. | 600/29 |
| 5,513,659 | 5/1996 | Buuck et al. . | |
| 5,701,916 | 12/1997 | Kulisz et al. | 600/29 |

FOREIGN PATENT DOCUMENTS

| | | |
|---|---|---|
| 0 265 207 | 10/1987 | European Pat. Off. . |
| 2 595 564 | 3/1986 | France . |
| 97/06758 | 2/1997 | WIPO . |

Primary Examiner—John P. Lacyk
Attorney, Agent, or Firm—Cesari and McKenna, LLP

[57] ABSTRACT

A urethral valve system includes a valve balloon that inflates to provide continence and deflates to allow urine to flow around the balloon and an attached catheter that extends through the urethra, and out of the body through the meatus. The urine cleanses the valve balloon, the catheter and the urethra of bacteria, and thus, minimizes infection. The catheter includes a check valve at the end that is accessible to the user. To inflate the balloon, the user attaches to the check valve a small pump that supplies air or a liquid such as water to inflate the balloon. To deflate the balloon, the user manipulates the check valve to allow the water or air to drain from the balloon. The valve balloon may be positioned in the bladder. To retain the system in the bladder when urine flows around the balloon and the catheter, the balloon deflates to a shape that is wider than the diameter of the neck of the bladder. Alternatively, the system may include an anchoring device, such as rubber fingers that extend from the base of the balloon beyond the neck of the bladder. The valve balloon may also be positioned in the urethra. The system then includes an anchoring device that is positioned in the bladder to hold the valve balloon in its deflated state in the urethra against the flow of urine through the urethra and around the balloon and the attached catheter. The valve system may further include an everting mechanism that provides non-irritating delivery of the valve balloon and/or the anchoring device.

32 Claims, 9 Drawing Sheets

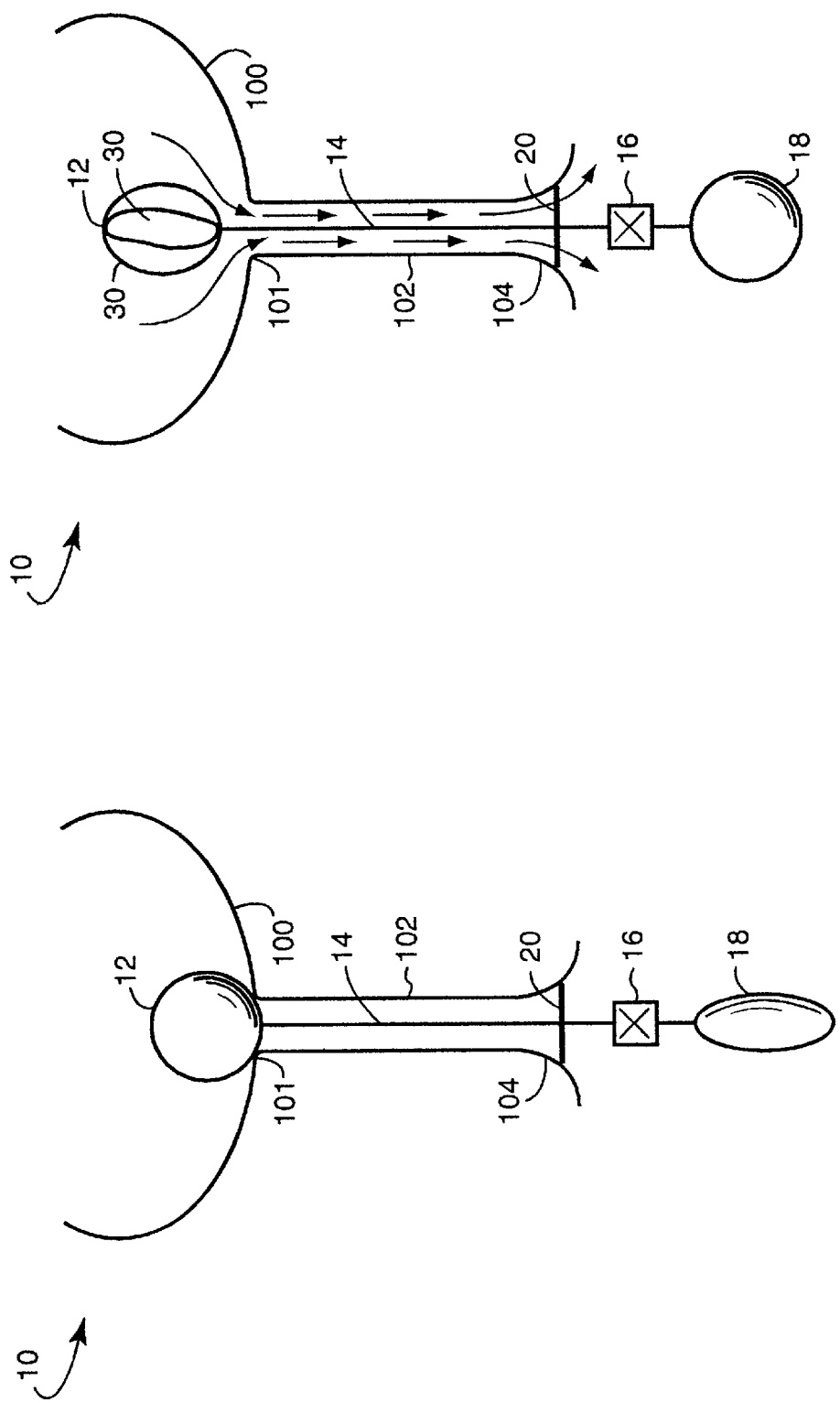

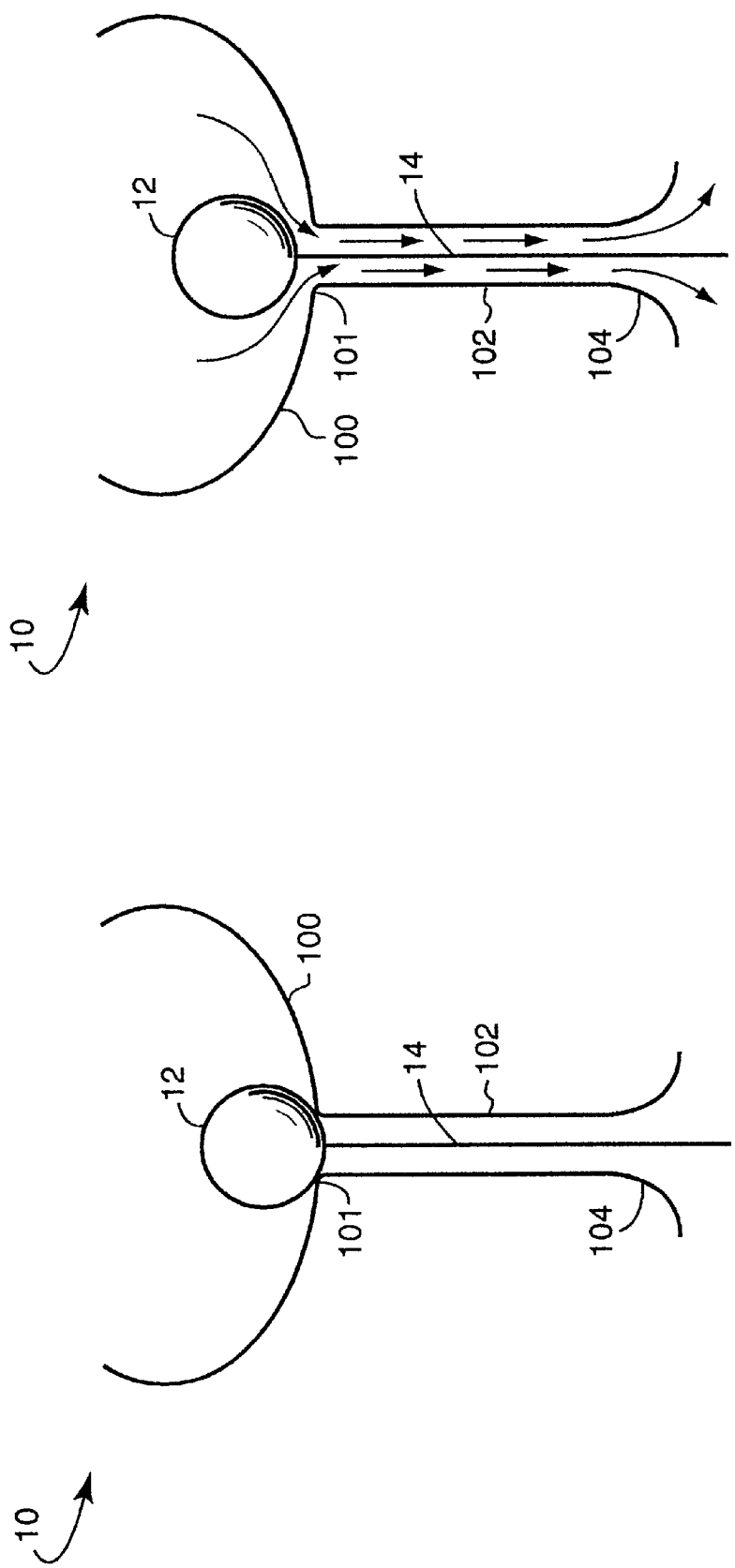

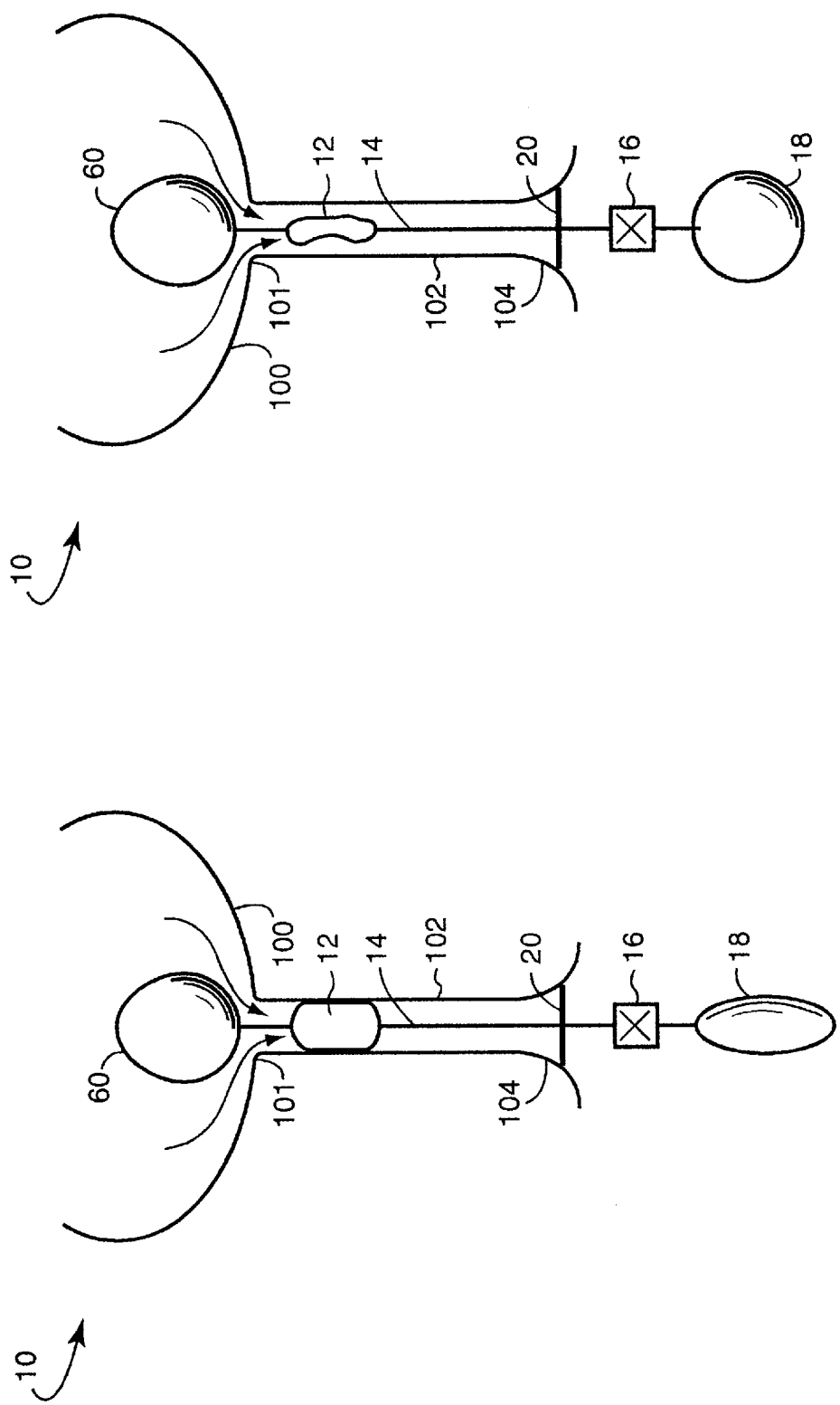

FLOW-AROUND VALVE

FIELD OF THE INVENTION

This invention relates generally to devices that control incontinence and, more particularly, to urethral valves.

BACKGROUND OF THE INVENTION

Incontinence is a serious problem for many people and, in particular, for many females. Adult diapers may be used to capture leaking urine, or alternatively, urethral plugs or valves may be used to provide continence. Urethral plugs and values are positioned in the urethra to block urine flow. The plug is removed from the urethra for urination. The valve remains in place and opens to allow urine to flow through the valve, and out of the body.

The urethral plug is used once and then thrown away. After voiding, a new plug must be inserted to again provide continence. Over time, with the repeated insertion and removal of the plugs, the lining of the urethra may become irritated.

Each time a plug is inserted, it carries bacteria from the meatus and the distal end of the urethra into the proximal end of the urethra. The bacteria may infect the urethra, particularly if the lining is irritated. Further, the bacteria may migrate up into and infect the bladder.

The urethral valve remains in the urethra over some period of days. The typical valve extends through the urethra to the outside of the body, where a mechanism for opening the valve is accessible to the user. The valve thus provides a path for bacteria to travel from the meatus and the distal end of the urethra to the proximal end of the urethra and the bladder. Further, the insertion of the valve into the urethra often irritates the lining of the urethra, and thus, promotes bacterial growth.

SUMMARY OF THE INVENTION

An improved urethral valve system includes a valve balloon that inflates to provide continence and in certain embodiments deflates to allow urine to flow around the balloon. A small-diameter catheter is attached to the balloon and extends through the urethra to provide access to the balloon from outside the body. When the urine flows around the balloon, the urine also flows around the catheter and through the urethra, and out of the body through the meatus. The urine cleanses the valve balloon, catheter and the urethra of bacteria, and thus, minimizes infection. In an alternative embodiment the valve balloon remains inflated during urination, and is moved from a position in which it blocks urine flow through the neck of the bladder to a position in which urine flows around the balloon, out of the neck of the bladder, around the catheter and through the urethra.

The valve system may be anchored in the bladder, to prevent the system from being drawn from the body by the flow of urine. The anchor may be, for example, a balloon, which may be either the same balloon that provides continence or a second balloon. If a single balloon is used both to anchor the system and provide continence, the balloon may deflate to a shape that retains the balloon in the bladder against the flow of urine. Alternatively, the system may include a mechanical means to hold the deflated balloon in the bladder, such as, for example, rubber fingers that extend from the base of the balloon beyond the neck of the bladder.

The valve balloon may instead be positioned within the urethra, with an anchoring mechanism positioned in the bladder to hold the deflated valve balloon in place during urination.

The catheter runs from the valve balloon through the urethra to the outside of the body, and includes a check valve at the end that is accessible to the user. To inflate the balloon, the user attaches to the check valve a small pump that supplies air or a liquid such as water to inflate the balloon. To deflate the balloon, the user manipulates the check valve to allow the water or air to drain from the balloon. The catheter has a small diameter, since urine flows around the catheter and not through it.

The valve system preferably includes an everting mechanism that provides non-irritating delivery of the valve and/or anchoring balloons to the body. An everted membrane unrolls to provide a path through the urethra for the balloons, to prevent irritation of the lining of the urethra. The everting mechanism also prevents bacteria from being drawn from the meatus and distal end of the urethra into the proximal end of the urethra and into the bladder.

BRIEF DESCRIPTION OF THE DRAWINGS

The invention description below refers to the accompanying drawings, of which:

FIG. 3A is an illustration of a third embodiment of a urethral valve system constructed in accordance with the invention;

FIG. 3B is an illustration of the third embodiment of the urethral valve system allowing urination;

FIG. 5A is an illustration of a fifth embodiment of a urethral valve system constructed in accordance with the invention;

FIG. 5B is an illustration of the fifth embodiment of the urethral valve system allowing urination;

FIG. 6A is an illustration of a sixth embodiment of a urethral valve system constructed in accordance with the invention;

FIG. 6B is an illustration of the sixth embodiment of the urethral valve system allowing urination;

DETAILED DESCRIPTION OF ILLUSTRATIVE EMBODIMENTS

Figure 1B:
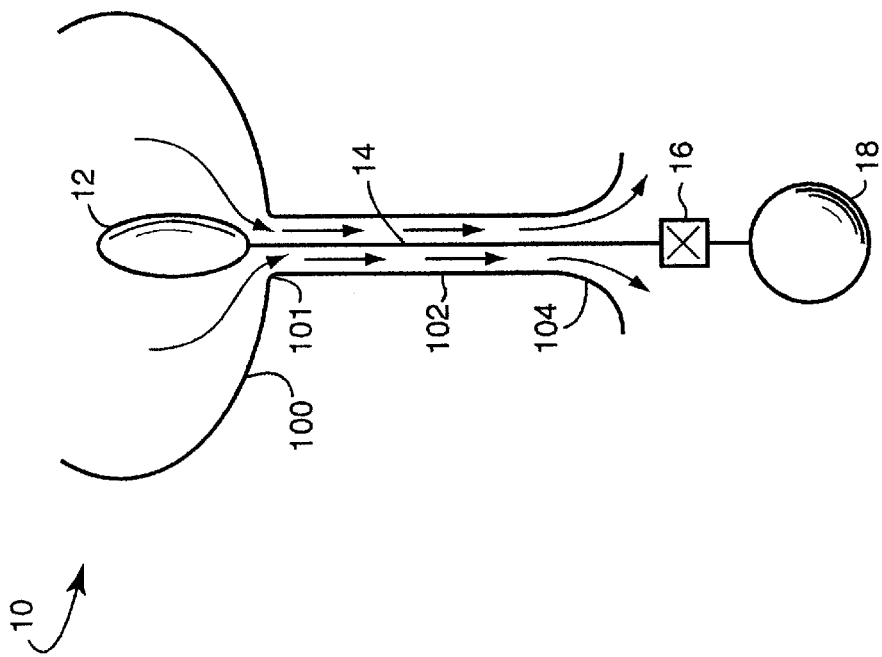
FIG. 1B is an illustration of the first embodiment of the urethral valve system allowing urination.
Figure 1A:
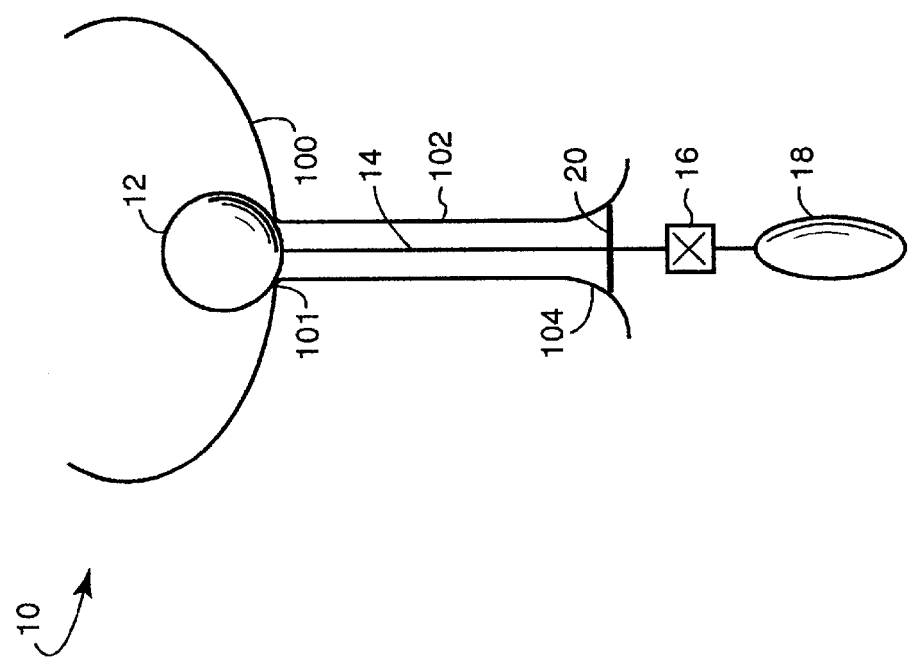
FIG. 1A is an illustration of a first embodiment of a urethral valve system constructed in accordance with the invention providing continence.

Referring to FIGS. 1A and 1B, a urethral valve system 10 includes a valve balloon 12 that is positioned in a bladder 100 to obstruct the flow of urine from the bladder. The diameter of the balloon 12 must be large enough essentially to seal the neck 101 of the bladder 100 and prevent urine flow from the bladder. A small-diameter catheter 14 attaches to the balloon 12 and extends through the urethra 102 and past the meatus 104. A check valve 16, which is closed to retain within the system the substance, such as air or water, that is used to inflate the balloon 12, extends slightly below the meatus 104. A pump 18, which is removably attached to the check valve 16, provides, for example, the water to the system. When the balloon is inflated, as depicted in FIG. 1A, the balloon provides continence.

For urination, a user deflates the balloon 12 through the check valve 16. As depicted by the arrows in FIG. 1B, when the balloon 12 is deflated urine flows around the balloon, through the neck 101 of the bladder 100, through the urethra 102 and around catheter 14, and out of the meatus 104. The urine flow cleanses the balloon 12 and the catheter 14 of bacteria in the same way that the body naturally cleanses the urethra, and thus minimizes the chances for infection from upwardly migrating bacteria.

The balloon 12 and the catheter 14 may also be coated with an antibacterial coating, to prevent colonization.

As depicted FIG. 1B, the pump 18 captures the water and retains it for use in re-inflating the balloon 12. The user may instead release the water from the system 10, and use fresh water to re-inflate the balloon.

The balloon is deflated for insertion into and removal from the bladder. Once deflated, the balloon is removed by gently pulling on the catheter 14.

For additional protection against the upward migration of both the system 10 and bacteria, a meatal collar 20 may be positioned slightly above the check valve 16. Further, the meatal collar 20, like the other system components, may be coated with an anti-bacterial coating to prevent colonization.

The balloon 12 and the catheter 14 may be made of any inflatable, non-reactive material, such as silicon. The catheter 14 has a small diameter since urine flows around the catheter rather than through the catheter.

Figure 2B:
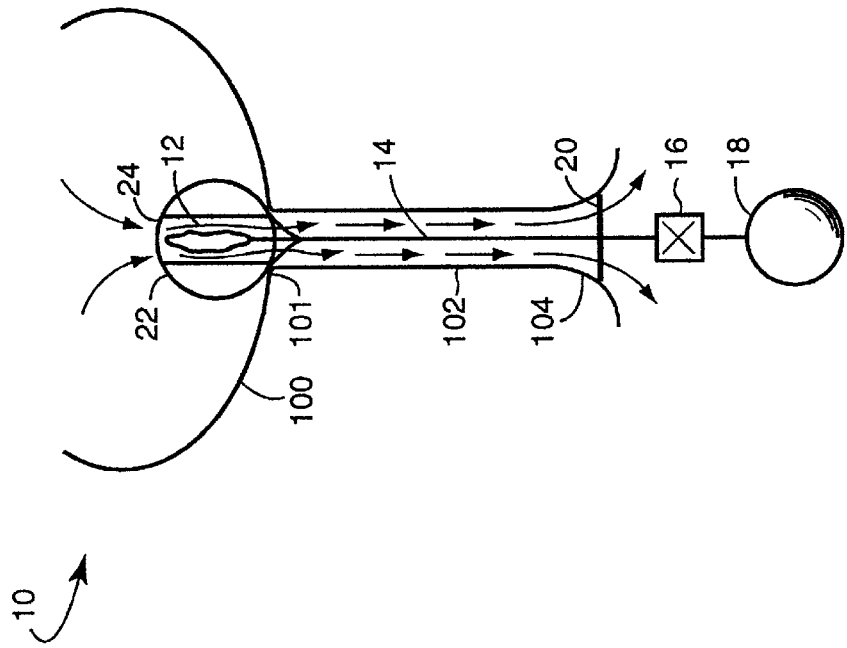
FIG. 2B is an illustration of the second embodiment of the urethral valve system allowing urination.
Figure 2A:
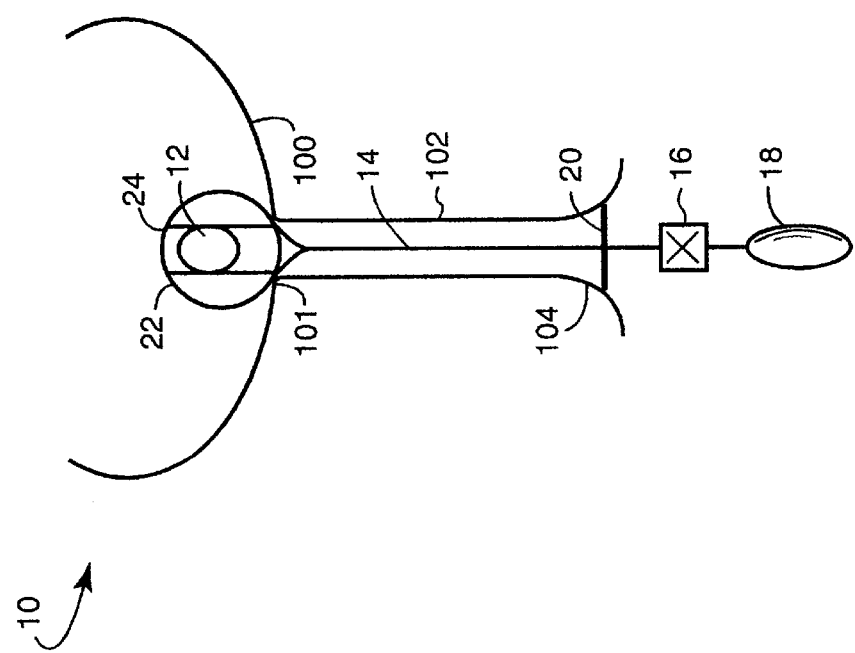
FIG. 2A is an illustration of a second embodiment of a urethral valve system constructed in accordance with the invention.
Figure 3D:
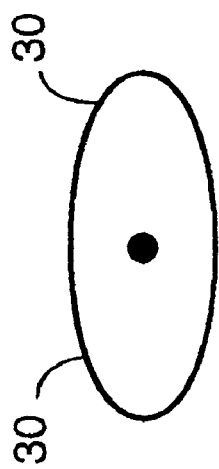
FIGS. 3C–D are top views of a component of the system of FIG. 3B.
Figure 3C:
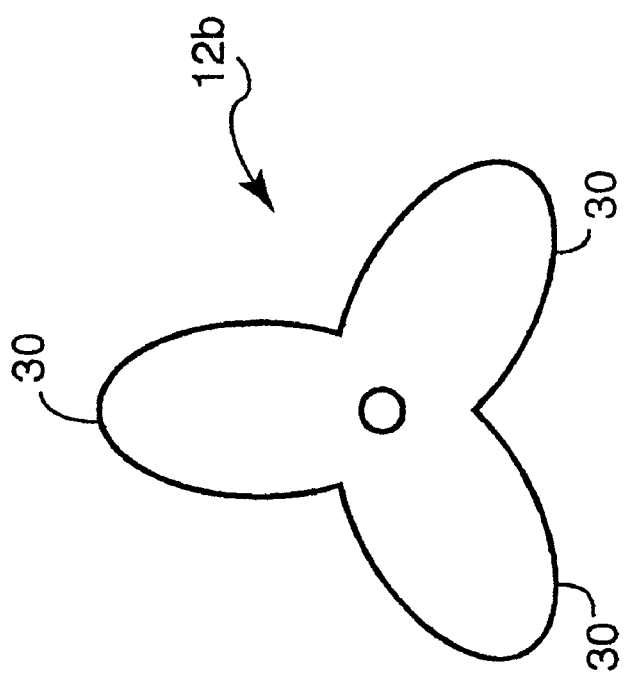

FIGS. 2A and 2B depict a second embodiment of the urethral valve system. In this embodiment, the valve balloon 12 is attached to a second, fixation balloon 22, which is included in the system to anchor it within the bladder 100. The fixation balloon in its inflated state, has a diameter that is larger than the neck 101 of the bladder 100, to ensure that the system will not be pulled from the bladder by the flow of urine. The fixation balloon 22 includes a channel 24 that houses the valve balloon 12. The valve balloon may be attached to the fixation balloon by, for example, webbing (not shown) through which urine can readily flow.

When the valve balloon 12 is inflated, the channel 24 is sealed to provide continence. When the valve balloon is deflated, as depicted in FIG. 2B, the channel 24 is opened and urine flows through the channel and around the valve balloon 12. The fixation balloon remains inflated during urination and holds the system in position against the flow of urine. As discussed above, the urine flow cleanses bacteria from the balloon 12 and the catheter 14, which comes in contact with the meatus 104 and the distal end of the urethra. The cleansing minimizes the upward migration of bacteria.

FIGS. 3A–3D depict a third embodiment of the urethral valve system. In this embodiment, the valve balloon 12 acts also as the anchoring mechanism. There is thus no need for the fixation balloon 22 (FIG. 2A). In this embodiment, the valve balloon 12 deflates into a shape 12b or 12c that includes one or more elongated arms 30. Urine can then flow around the arms 30, through the neck 101 of the bladder 100, around the catheter 14 and through the urethra 102, and out of the meatus 104.

The arms 30 have a span that is longer than the width of the neck 101 of the bladder 100, and they thus, retain the balloon 12 in the bladder against urine flow. The arms 30 are also flexible so that the balloon can be removed from the bladder by gently pulling on the catheter 14.

Figure 4B:
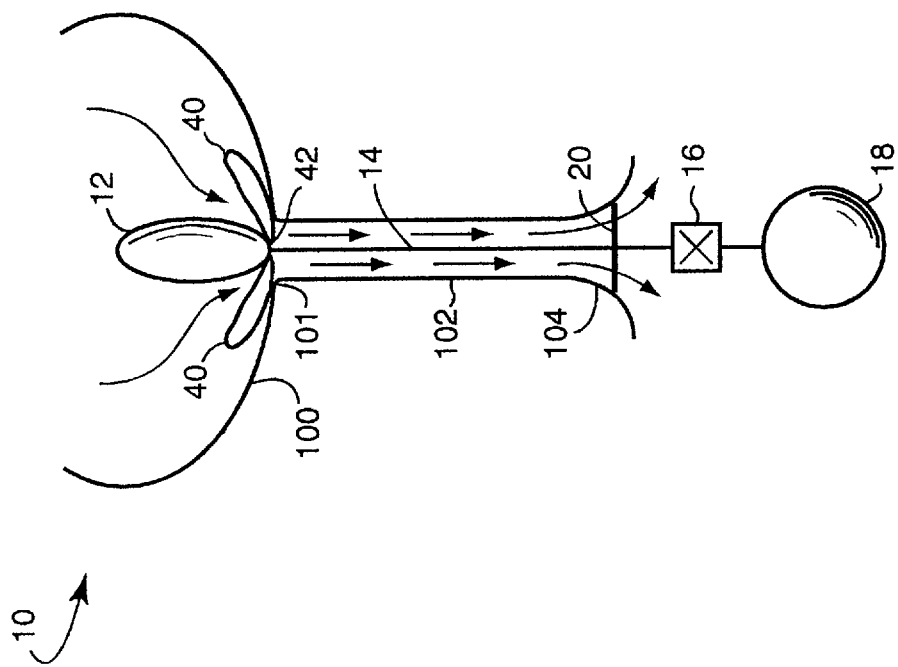
FIG. 4B is an illustration of the fourth embodiment of the urethral valve system allowing urination.
Figure 4A:
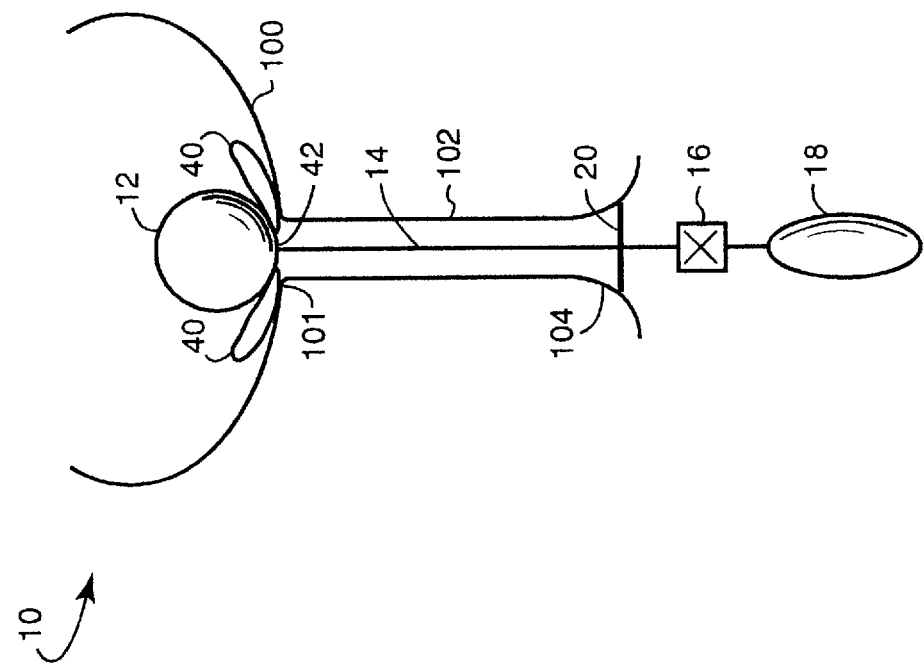
FIG. 4A is an illustration of a fourth embodiment of a urethral is valve system constructed in accordance with the invention.

Referring now to FIG. 4, a fourth embodiment of the urethral valve system includes flexible fixation tabs 40 that extend outwardly from a base 42 of the balloon 12. When the balloon 12 is deflated, the tabs 40 hold the balloon in place at the neck 101 of the bladder 100. Urine then flows around the balloon and the tabs, out of the bladder, around the catheter 14 and through the urethra, and out of the body through the meatus.

In FIG. 5, the catheter 14 is stiffened somewhat, so that a user can move the valve balloon 12 away from the neck 101 of the bladder. Urine can then flow out of the neck of the bladder 100 and through the urethra 102. To reposition the valve balloon 12 in the neck of the bladder the user then gently pulls on the catheter 14.

Figure 7:
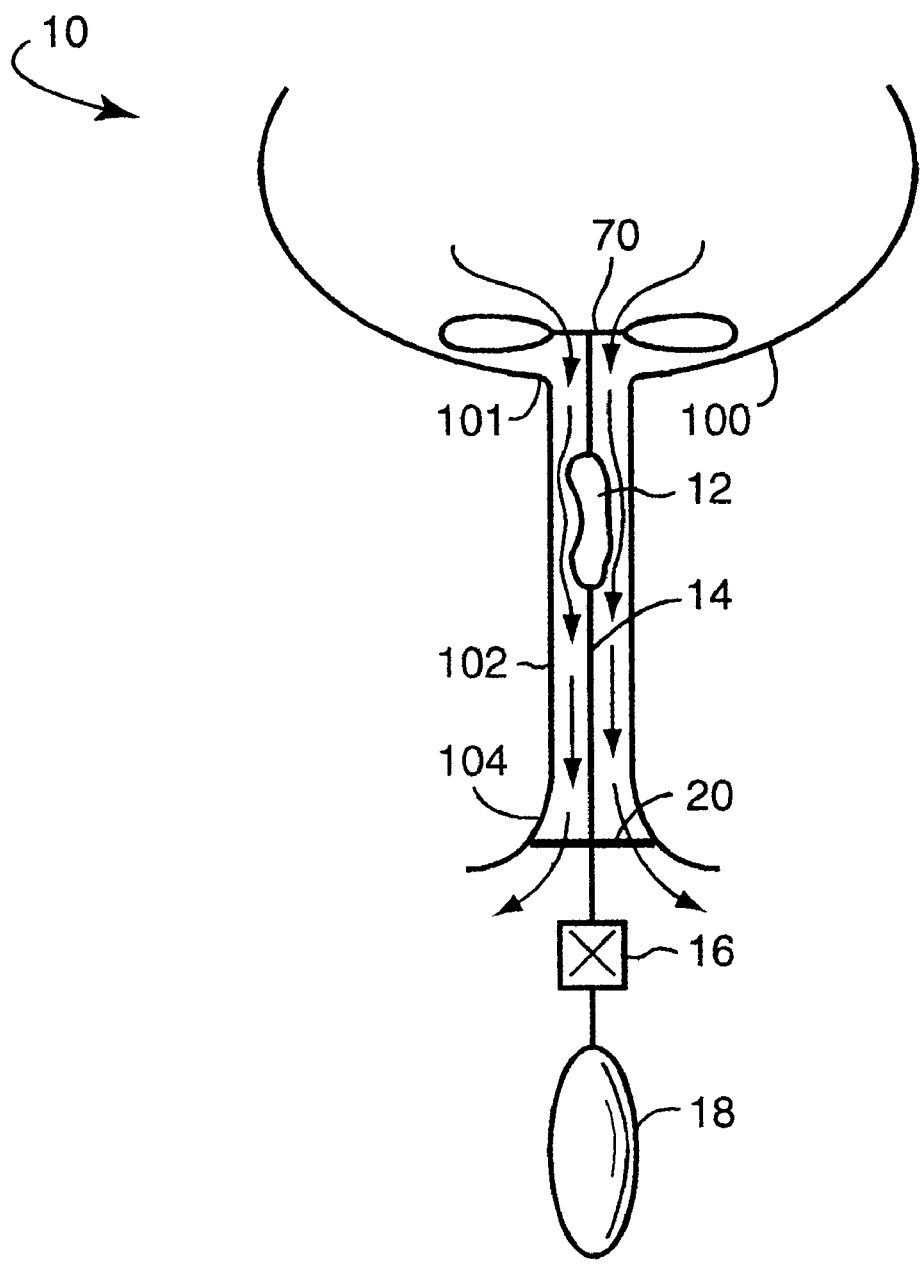
FIG. 7 is an illustration of a seventh embodiment of the urethral valve system allowing urination.

As shown in FIGS. 6 and 7, the valve balloon 12 may be positioned in the urethra 102. When the valve balloon 12 is inflated, it provides continence by blocking the flow of urine in the urethra. When the balloon 12 is deflated, urine flows around the balloon and the attached catheter 14 and through the distal end of the urethra 102 and out of the body through the meatus 104.

Different types of fixation devices may be used to retain the system in place against the flow of urine. For example, a second balloon 60 may be positioned in the bladder, as shown in FIG. 6. Alternatively, as depicted in FIG. 7, foldable arms 70, which are inserted and then unfolded in the bladder 100, may be used to anchor the system.

Figure 8:
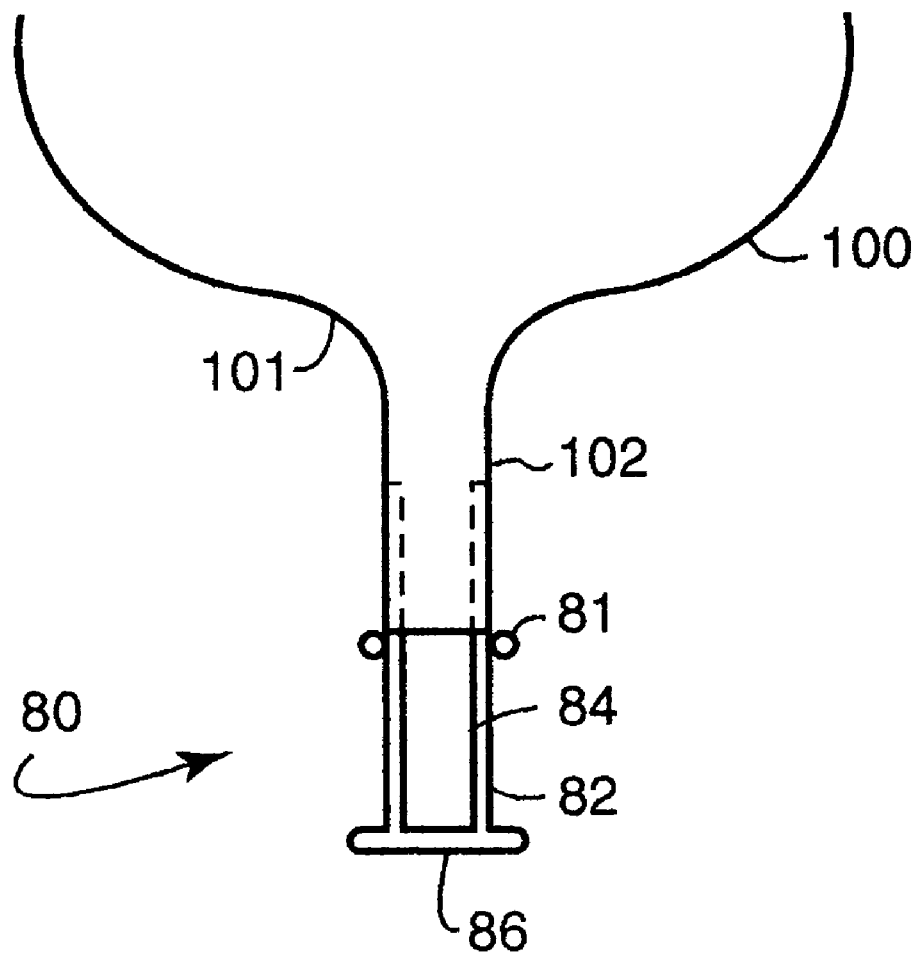
FIG. 8 is an illustration of an everting mechanism that may be used with the urethral valve system of FIGS. 1–7.

FIG. 8 depicts an everting mechanism 80 that may be used for introduction of the valve system 10 (FIGS. 1–7) into the body through the urethra. The everting mechanism 80 includes an introducing device 82, such as, for example, a tube, that a user inserts into the distal end of the urethra 102 up to a stop 81. The tube contains an everted membrane 84 with one end held by the stop. The membrane 84 unrolls, as depicted by dotted lines, as an advancing device 86 is pushed deeper into the urethra. The unrolled membrane then provides a path through which the valve system may be inserted, without coming into contact with the lining of the urethra. After the system is fully inserted, the membrane 84 is removed from the body.

There is essentially no relative motion between the membrane 84 and the walls of the urethra as the membrane unrolls. Accordingly, the lining of the urethra is not irritated by the insertion of the membrane, or the introduction of the valve system through the membrane.

Further, the surface of the membrane that comes in contact with the lining of the urethra does not come in contact with the distal end of the urethra. Accordingly, bacteria from the distal end of the urethra is not carried deeper into the urethra or into the bladder by either the membrane, or the valve system that is introduced through the membrane.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. A urethral valve system for controlling urine flow from a bladder through a urethra, the valve system including:
   A. a valve balloon that is positioned in the body and inflates to prevent urine flow and deflates and remains in the body to allow urine to flow around the balloon and through the urethra; and
   B. a catheter that connects to the balloon at a first end and extends through the urethra to provide access to the balloon from outside of the body for inflation and deflation of the balloon.

2. The urethral valve system of claim 1 wherein the valve balloon is positioned within the bladder.

3. The urethral valve system of claim 2 further including a fixation balloon that is positioned in the bladder to hold the valve system in place against urine flow, the fixation balloon including an interior channel that houses the valve balloon.

4. The urethral valve system of claim 2 wherein the valve balloon deflates to a shape that holds the balloon in the bladder against urine flow.

5. The urethral valve system of claim 2 further including a flexible anchoring mechanism for holding the deflated valve balloon in the bladder against urine flow.

6. The urethral valve system of claim 5 wherein the anchoring mechanism includes one or more flexible fingers that extend from a base of the valve balloon along the interior of the bladder.

7. The urethral valve system of claim 1 further including a check valve at the second end of the catheter, the check valve opening to allow a substance to be inserted into the valve balloon in order to inflate the balloon and closing to contain the substance, the check valve again opening to release the substance contained in the valve balloon in order to deflate the balloon.

8. The urethral valve system of claim 1, wherein
   i. the valve balloon is positioned within the urethra, and
   ii. the valve system further includes a fixation balloon, the fixation balloon being positioned within the bladder to hold the valve balloon in place against urine flow.

9. The urethral valve system of claim 8 further including a check valve at the second end of the catheter, the check valve opening to allow a substance to be inserted into the valve balloon in order to inflate the balloon and closing to contain the substance and keep the valve balloon inflated, the check valve opening to release the substance contained in the valve balloon in order to deflate the balloon.

10. The valve system of claim 1 further including an anchoring mechanism that retains the deflated valve balloon in the body against urine flow.

11. The valve system of claim 10 wherein the anchoring mechanism is flexible.

12. The urethral valve system of claim 1, wherein
   i. the valve balloon is positioned within the urethra, and
   ii. the valve system further includes an anchoring mechanism that holds the valve balloon in place against urine flow.

13. The urethral valve system of claim 12, wherein the anchoring mechanism is positioned in the bladder.

14. An incontinence device including:
   A. a balloon that has a deflated state and an inflated state, the balloon being positioned in the body to prevent urine flow when the balloon is in the inflated state and remaining in position in the deflated state to allow urine to flow around the balloon and out of the body;
   B. a catheter having a first end and a second end, the catheter connecting at the first end to the balloon and providing access to the balloon from outside the body at the second end; and
   C. an everting mechanism for inserting the balloon and the catheter into the body through the urethra when the balloon is in the deflated state;
wherein a substance is introduced into the balloon through the catheter to inflate the balloon after the balloon has been positioned in the body by the everting mechanism.

15. The incontinence device of claim 14 further including a check valve at the second end of the catheter, the check valve opening to allow a substance to be inserted into the balloon in order to inflate the balloon and closing to contain the substance, the check valve again opening to release the substance contained in the balloon in order to deflate the balloon.

16. A urethral valve system for controlling urine flow from a bladder through a urethra, the valve system including:
   A. a valve balloon that inflates to prevent urine flow and deflates and remains within the body to allow urine to flow around the balloon and through the urethra; and
   B. a catheter that connects to the balloon at a first end to provide access to the balloon from outside the body for the inflating and deflating of the balloon, the catheter extending through the urethra and when urine flows through the urethra the urine flows around the catheter.

17. The urethral valve system of claim 16 further including a check valve at the second end of the catheter, the check valve opening to allow a substance to be inserted into the valve balloon in order to inflate the balloon and closing to contain the substance, the check valve again opening to release the substance contained in the valve balloon in order to deflate the balloon.

18. The urethral valve system of claim 17 wherein the valve balloon is positioned within the bladder.

19. The urethral valve system of claim 18 further including a fixation balloon that is positioned in the bladder to hold the valve system in place against urine flow, the fixation balloon including an interior channel that houses the valve balloon.

20. The urethral valve system of claim 18 wherein the valve balloon deflates to a shape that holds the balloon in the bladder against urine flow.

21. The urethral valve system of claim 18 further including a flexible anchoring mechanism for holding the deflated valve balloon in the bladder against urine flow.

22. The urethral valve system of claim 21 wherein the anchoring mechanism includes one or more flexible fingers that extend from a base of the valve balloon along the interior of the bladder.

23. The urethral valve system of claim 17, wherein
   i. the valve balloon is positioned within the urethra, and
   ii. the valve system further includes a fixation balloon, the fixation balloon being positioned within the bladder to hold the valve balloon in place against urine flow.

24. A method of controlling urine flow through the urethra, the method including the steps of:
   A. inserting an inflatable valve into the body;
   B. inflating the valve to block urine flow through the urethra;
   C. deflating and retaining the valve in the body to allow urine to flow around the valve and out through the urethra.

25. The method of claim 24 wherein the step of inserting the valve includes positioning the valve in the urethra.

26. The method of claim 24 wherein the step of inserting the valve includes positioning the valve in the bladder.

27. The method of claim 24 wherein the steps of inflating the valve and deflating the valve include using a catheter to provide access to the valve.

28. An incontinence device including:
   A. a fixation balloon for positioning in the bladder, the fixation balloon remaining in place during continence and voiding and including a channel through which urine flows from the bladder and through the urethra;
   B. blocking means positioned in the channel, the blocking means having a first state and a second state and when in the first state blocking urine flow through the channel and the urethra and when in the second state allowing urine to flow around said blocking means and through the channel and the urethra.

29. The incontinence device of claim 28 wherein the blocking means is a valve balloon and the first state is inflated and the second state is deflated.

30. The incontinence device of claim 28 wherein the blocking means is a balloon and in the first state the balloon is in a first position and seals the channel against urine flow and in the second state the balloon is in a second position in which the channel is unsealed and urine flows around the balloon and through the channel and the urethra.

31. The incontinence device of claim 28 further including a catheter for providing access to the fixation balloon from outside the body, the catheter allowing the fixation balloon to deflate for removal from the body and to inflate for retention in the body.

32. The incontinence device of claim 29 further including a catheter for providing access to the blocking means from outside the body, the catheter allowing the blocking means to repeatedly go from the first state to the second state for voiding and from the second state to the first state for continence.

* * * * *